(12) United States Patent
Heath

(10) Patent No.: US 7,993,298 B2
(45) Date of Patent: Aug. 9, 2011

(54) HOSE SET

(75) Inventor: Andy Heath, Gloucester (GB)

(73) Assignee: W.O.M. World of Medicine A.G. (DE)

( * ) Notice: Subject to any disclaimer, the term of this patent is extended or adjusted under 35 U.S.C. 154(b) by 0 days.

(21) Appl. No.: 11/586,419

(22) Filed: Oct. 25, 2006

(65) Prior Publication Data

US 2008/0294090 A1 Nov. 27, 2008

(30) Foreign Application Priority Data

Oct. 28, 2005 (DE) .................. 10 2005 052 122

(51) Int. Cl.
*A61M 37/00* (2006.01)
(52) U.S. Cl. .......................... 604/26; 604/23
(58) Field of Classification Search ............... 604/19–26
See application file for complete search history.

(56) References Cited

U.S. PATENT DOCUMENTS

| | | | |
|---|---|---|---|
| 5,098,375 A | 3/1992 | Baier | 604/23 |
| 5,139,478 A * | 8/1992 | Koninckx et al. | 604/26 |
| 6,632,194 B1 | 10/2003 | Mehner et al. | 604/26 |
| 2005/0038374 A1 | 2/2005 | Williams, Jr. et al. | |
| 2009/0082718 A1 * | 3/2009 | Mantell | 604/26 |

FOREIGN PATENT DOCUMENTS

| | | |
|---|---|---|
| DE | 3922746 C1 | 8/1990 |
| DE | 19955847 C1 | 8/2001 |
| EP | 0 633 039 | 7/1994 |
| EP | 0837551 A2 | 5/1998 |
| EP | 0684850 B1 | 5/1999 |
| EP | 1576971 A1 | 1/2005 |
| WO | WO 94/01154 | 1/1994 |
| WO | 2005028012 | 3/2005 |

* cited by examiner

*Primary Examiner* — Theodore Stigell
*Assistant Examiner* — Imani Hayman
(74) *Attorney, Agent, or Firm* — Mayer & Williams PC; Mark K. Young

(57) ABSTRACT

The invention relates to a hose set for a device (1) for insufflation of gas into a human or animal body, comprising a first hose portion (2) including a first port (3) and a second port (4), said first port being connectable to the device (1) for insufflation, comprising a second hose portion (5) including a third port (6) and a fourth port (7), said fourth port (7) being connectable to an insufflation instrument (8), wherein said second port (4) comprises a first connecting element (9) and said third port (6) comprises a second connecting element (10), said first connecting element (9) and said second connecting element (10) being mechanically complementary with respect to each other, by means of said connecting elements (9, 10) said second port (4) and said third port (6) being connectable with each other in a gas-tight manner, and wherein said second or said third port (6) comprises a sterile filter element (11), which spans the inner cross section of said third port (6).

15 Claims, 2 Drawing Sheets

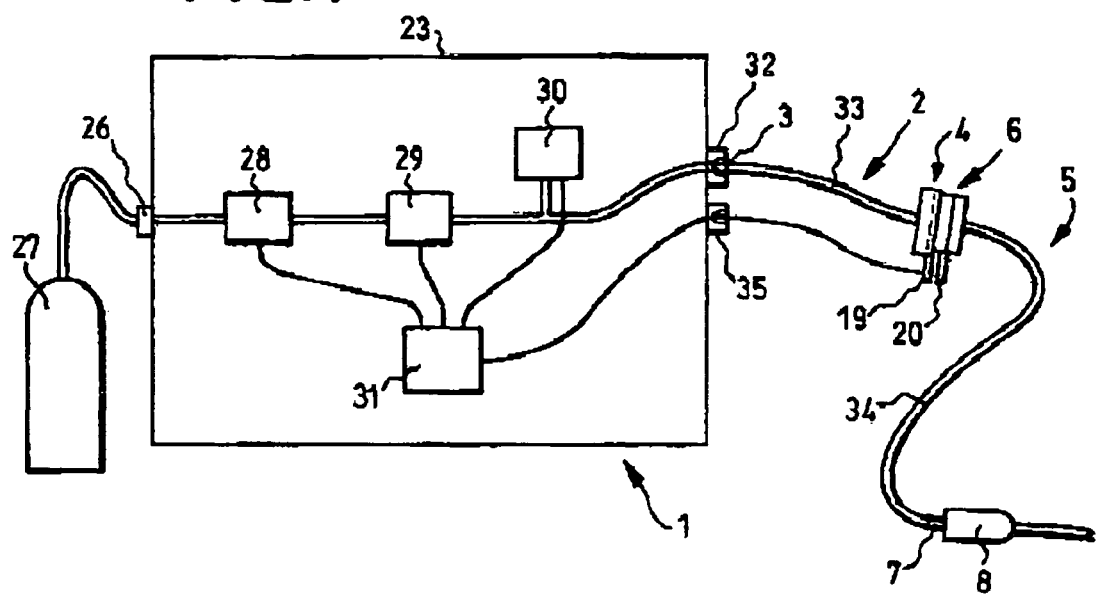
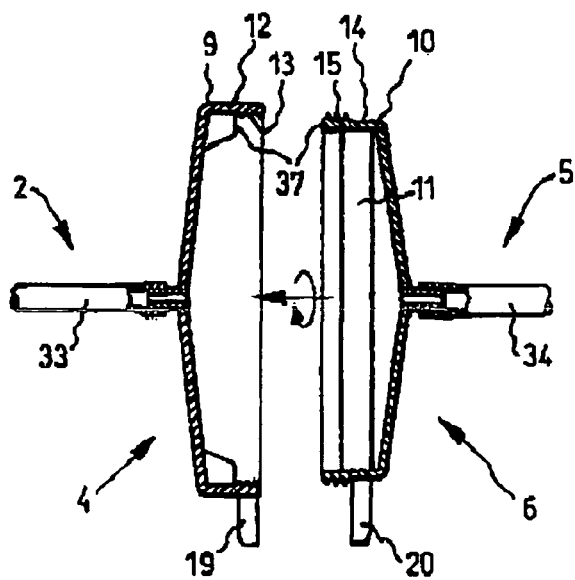

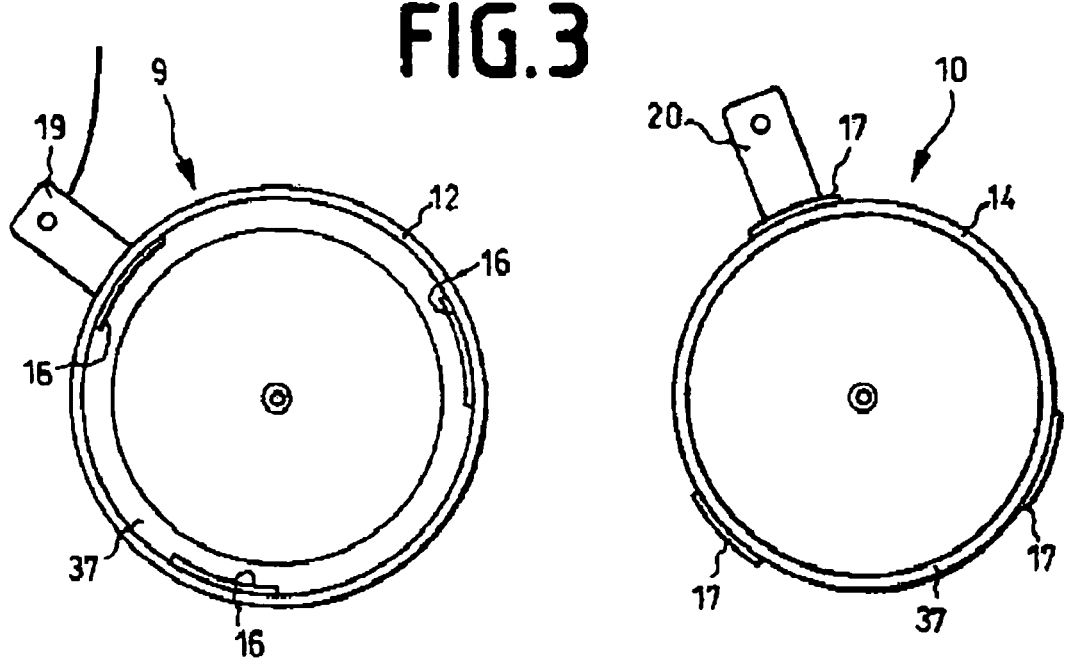
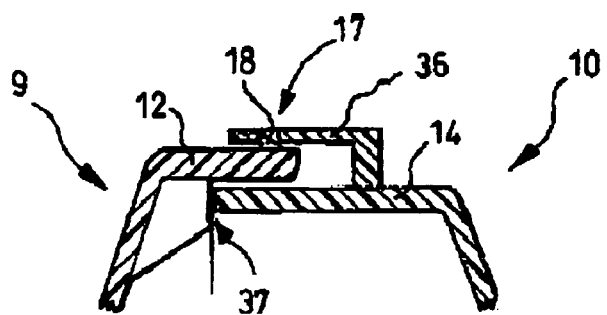

HOSE SET

FIELD OF THE INVENTION

The invention relates to a hose set for a device for insufflation of gas into a human or animal body comprising a first port, which can be connected to the device for insufflation, and comprising a further port, which can be connected to an insufflation instrument, wherein the hose set comprises a sterile filter element, which spans the inner cross section. The invention further relates to a device for insufflation of gas comprising such a hose set.

BACKGROUND OF THE INVENTION

Hose sets of this kind are in particular used in the field of the endoscopy and laparoscopy. The type of gas typically employed is carbon dioxide, but other gases, if applicable with pharmaceutical additives, can of course also be used. As an insufflation instrument, a Veress needle may, for instance, be used.

From the document DE 3922746 C1 it is known in the art to employ a sterile filter between the insufflation instrument and the gas supply device. The sterile filter is inserted into the hose, which is provided between the gas supply device and the insufflation instrument. With these measures being insofar known in the art, it cannot be excluded with sufficient certainty that an operator will use no sterile filter at all or an already used one, with the consequence of a health risk for the patient.

From the document EP 0684850 B1, there is also known in the art a filter element, which is employed between the hose line and the gas source. This, too, is a usual filter element requiring separate handling and being double-sidedly connected.

From the document DE 19955847 C1, a device for the insufflation of gas is known in the art, wherein a sterile filter element is integrated in the hose set to be connected and represents part of the port of the hose set at the gas supply device.

In particular, a hose set according to document DE 19955847 C1 has in principle been tried and tested. With regard to the increasing cost pressures in the health sector, it is however desirable to be able to re-use at least parts of a hose set.

It is therefore an object of the present invention to provide a hose set for insufflation of gas, which can at least partially be re-used, and simultaneously maintain very high safety with regard to sterility.

SUMMARY OF THE INVENTION

One embodiment of the invention teaches a hose set for a device for insufflation of gas into a human or animal body, comprising a first hose portion including a first port and a second port, the first port being connectable to the device for insufflation, and a second hose portion including a third port and a fourth port, the fourth port being connectable to an insufflation instrument. The second port includes a first connecting element and the third port includes a second connecting element, the first connecting element and the second connecting element being mechanically complementary with respect to each other, by means of the connecting elements, the second port and the third port being connected with each other in a gas-tight manner, and wherein the third port comprises a sterile filter element, which spans the inner cross section of the third port. It is essential that in any case the second port is an integral component of the first hose portion and the third port is an integral component of the second hose portion. This means that the hoses cannot be removed from the respective ports during normal use. It is understood that the two connecting elements can be connected with each other in a gas-tight manner, if applicable by using a seal.

The hose set described herein is basically bipartite. The second hose portion comprising the sterile filter element is intended for replacement after every use. The first hose portion, however, can be re-used several times and is replaced, for instance, only every 24 hours. Thus, the complete hose set does not need to be replaced after every use, but only the second hose portion is replaced, thereby substantially reducing costs. Furthermore, the quantities of waste to be disposed of are considerably reduced.

Preferably, the second connecting element carries the sterile filter element, i.e. the sterile filter element is integral therein. The sterile filter element may extend over the full inner cross section of the second connecting element. It is, however, also possible that the sterile filter element extends over part of the inner cross section only, and the remainder of the inner cross section is closed by a gas-tight wall.

In detail, the connecting elements being complementary to each other may be adapted in different variants.

First, it is possible that one of the connecting elements is formed by a flange with an external thread and the other connecting element is formed by a flange with an internal thread being complementary to the external thread, and the flanges are connected with each other in a gas-tight manner by a screw fit in a final position.

Second, it may be provided that one of the connecting elements is formed by a flange with latching projections being spaced from each other and projecting inwardly, and the other connecting element is formed by a flange with holding projections extending in a radial direction, wherein the holding projections, relative to the peripheral direction of the flange, have a distance, which is larger than the length of the latching projections, and wherein the holding projections and the latching projections are engageable with each other by rotating the two flanges against each other into a final position and connect the flanges with each other in a gas-tight manner. Such a configuration of the connecting elements is also called a bayonet-type fit.

Third, it is possible that one of the connecting elements is formed by a flange having at least one latching recess provided in a section of the periphery of the flange, and the other connecting element is formed by a flange having at least one latching element provided in a section of the periphery, wherein the latching recess and the latching element are complementary with respect to each other and connect the flanges with each other in a gas-tight manner by latching in each other into a final position. In this embodiment, it is recommendable to provide several complementary latching recesses and latching elements, and to distribute them over the periphery of the flanges. The number of latching elements and latching recesses may be between two and ten, preferably three to five. In a specific embodiment of this variant, one of the connecting elements comprises a flange sleeve, into which the flange of the other connecting element can be inserted. On the inner side of the flange sleeve, a circumferential latching projection is provided, and on the outer periphery of the flange, a circumferential latching recess is provided. When inserting the components into each other, latching projection and latching recess will engage in a gas-tight manner. Of course, the flange sleeve may instead have on the inner side a circumferential latching recess, and the flange may have on its outer side a latching projection. The latching recesses and/or the latching element or latching projection may be formed from an elastic or plastic material, for instance a conventional polymeric material.

Finally, in another variant, one of the connecting elements may comprise a flange sleeve, the inner diameter of which is in the opening section larger than the outer diameter of the flange of the other connecting element and wherein the inner diameter of the flange sleeve, relative to the direction of insertion of the flange of the other connecting element, reduces to an inner diameter, which is smaller than the outer diameter of the flange of the other connecting element, wherein at least one of the components, flange sleeve and/or flange, is formed from a plastic or elastic material. A kinematic reversal of the above is provided, when one of the connecting elements comprises a flange sleeve with a cylindrical inner wall, wherein the outer diameter of the flange, relative to the direction of insertion of the flange of the other connecting element, reduces from an outer diameter, which is larger than the inner diameter of the flange sleeve, to an outer diameter, which is smaller than the inner diameter of the flange sleeve. Of course it is also possible that the inner diameter of the flange sleeve and the outer diameter of the flange are conical in the above meaning. The reduction of the inner diameter or of the outer diameter may be continuous. When firmly inserting the flange into the flange sleeve, in each of these variants a friction fit is obtained, which holds the two connecting elements together. As materials, in principle all conventional polymeric materials can be used, since they have the required elasticity or plasticity. It is however recommended not to use polymeric materials having very low friction values, such as Teflon, in order that the friction fit is sufficient for a safe connection. The conicity of the inner side of the flange sleeve or of the outer diameter of the flange may be in the range from 0.1° to 5°, preferably 0.1° to 2°, relative to the central axis of the flange sleeve.

It is common to the above variants of the connecting elements that during the connection process, the flanges are moved in an axial direction into each other or towards each other. Thereby, annular sealing surfaces in the connecting elements can be brought into contact with each other, thus the gas tightness of the connection against the environment being secured. For this purpose, in at least one of the connecting elements an annular seal, for instance made from an elastomeric material, can be provided.

The firm connection of the sterile filter element in the second hose portion secures that by removing the sterile filter element, simultaneously the second hose portion connected therewith is removed, and vise versa. Further, a use of the hose set without the sterile filter element is not possible.

As a sterile filter element, for instance a membrane filter with a flow capacity of 5 to 100 l/min, preferably of 16 to 60 l/min, can be provided. As material, for instance PTFE having a pore size of 1 to 5 µm, preferably approx. 3 µm, can be used. Such membrane filters have a filtration efficiency of 99.9998%. In principle, however, all other filter element types causing sufficient germ retention and having a sufficiently low gas flow resistance can also be employed.

The first port and the fourth port may be commercially available plug-in, screw-in or bayonet-type ports, and corresponding complementary ports are provided in the gas supply device or the insufflation instrument.

In a particularly preferred embodiment, either the first connecting element, in the section of the periphery of its flange, or a gas supply device, to which the hose set is connected, carries an electric reading unit, and the second connecting element, in the section of the periphery of its flange, carries a machine readable identity element, wherein the identity element and the reading unit are arranged, in the final position of the two flanges, immediately opposite to each other. When the first connecting element and the second connecting element are connected with each other, or when the hose set is connected with the gas supply device, therefore the reading unit can read out the identity element. An identity element is a feature containing information about the sterile filter element. Machine readable identity elements are known and can be used for this invention in most various embodiments. Examples are: bar code, magnetic strip, microchip and hologram. In the case of the magnetic strip and the microchip, it is also possible to modify and/or complement the information content of the identity element, then the reading unit having in addition to be adapted in a suitable way as a write unit, or an additional write unit having to be provided. In the case of the bar code, the reading unit is an optical scanner. In the case of the magnetic strip, the reading unit is a magnetic reading head, which if applicable may also be used as a writing head. In the case of the microchip, the reading unit is a contact field contacting assigned contact fields of the identity element, if the connecting elements are connected. In the case of the hologram, the reading unit comprises a source of coherent light and a suitable optical sensor system. In the above specific variants, the reading unit will normally be arranged at the first connecting element. Furthermore, the identity element may be a transponder. Then the reading unit is a transponder scanning device. In this variant, the reading unit may not only be provided at the first connecting element, but alternatively or additionally also at the gas supply device, since reading is also possible over a distance of up to 0.5 m, even up to 1.0 m and more, depending on the employed transponder technology. In any case, a suitable transformation of the properties recorded by the reading unit into electrical signals takes place, which, if applicable after A/D conversion, are fed as information signals to a preferably digital evaluation unit. In the evaluation unit, the information read out by means of the reading unit from the identity element is evaluated, and the gas supply device is activated or blocked, depending to the result of this evaluation. For this purpose, the evaluation unit comprises memory elements, where the information as well as reference information can be stored or is permanently stored. In this embodiment, a deliberate or improper re-use of already used second hose portions can reliably be prevented by suitable measures in the evaluation unit. It is for instance possible that the identity element comprises a code element being different for every second hose portion (for instance coding a consecutive numbering). When a second hose portion is used for the first time, the code element is read in and stored in the evaluation unit as "actual", and it is checked by comparison based on code elements previously stored as "used" whether the actual individual code element has previously been read already. In the case of the actual first use this is not the case, and the gas supply is activated. The information of the actual code element is then (e.g. after removal of the second hose portion) stored as "used". If however the individual code element has previously been read in, i.e. is stored already as "used", it is no first use anymore of the respective second hose portion, and the evaluation unit then blocks the gas supply and generates acoustic or optical signals, if applicable. If e.g. a magnetic strip, a microchip and/or a transponder are used, during a first use alternatively or additionally a blocking code can be written into the identity element. If then a re-use of the second hose portion is tried, the evaluation unit identifies the blocking code read in by means of the reading unit, with the consequence mentioned above of an alarm signal and/or an inactivation of the gas supply device. It is secured, in this embodiment, that a re-use of a second hose portion is also not possible when using different apparatuses.

All in all, the embodiment of a machine readable identity element secures a very high operating reliability of the hose set according to the invention. It is not left to an operator whether or not an already used second hose portion could be used once again. A proper operation is only possible, if a new, i.e. unused second hose portion has been connected.

In an advantageous improvement of the invention, the identity element comprises a safety element. A safety element is a manually, visually or machine readable element, which is provided with a high safety against copying. Safety elements, also machine readable safety elements, are for instance widely known from the technique of stock and money bills and can correspondingly be used in conjunction with the present invention. A machine readable safety element is for instance formed by a hologram. Holograms can only be copied with relatively very high technological efforts, so that the application of counterfeited holograms for the purpose of the invention becomes economically unattractive. In the case of machine readable safety elements (in addition to holograms, there can for instance also be used magnetic safety elements etc.), an automatic blocking of the gas supply can be effected by the evaluation unit, if the safety element is lacking and/or does not meet the requirements, provided that the reading unit is arranged for reading the safety element and/or a separate safety element reading device is provided. By means of such a safety element, a substantially higher degree of safety for patients is achieved, since second hose portions of not authorized manufacturers, in particular cheap products of poorer quality, will not be accepted by the evaluation unit. An operator can thus only use second hose portions of the quality-controlled authorized manufacturers, in order to set the gas supply device into operation. A safety element may also be provided in the identity element as a safety code element.

The first connecting element may carry in the section of the periphery of its flange a first electrical port, and the second connecting element may carry in the section of the periphery of its flange a second electrical port, wherein with the second port a humidity sensor is arranged in the second hose portion and downstream the sterile filter element. In the final position of the connecting elements, the two electrical ports are contacted with each other. Further, a heating device electrically connected with the second port may be arranged in the second hose portion.

By a wire connection from the first electrical port to the device for insufflation, the humidity sensor can be read out and the heating device can be supplied with power.

With the first electrical port can be connected, irrespective of the above, a wire connection for the connection to the device for insufflation, by means of which the information read out from the identity element can be transmitted to the evaluation unit. Alternatively, this may however also take place in a wireless manner. Thus it is possible that with the first electrical port, a transmitter for the wireless transmission of data to the device for insufflation is electrically connected. This may be a radio transmitter or an IR transmitter.

In the embodiment comprising a liquid sensor, the following has to be noted. Filter units are or may be hydrophobic and insofar block liquids. These hydrophobic material properties are however guaranteed by the manufacturers for a certain period of time only. For safety reasons, it is therefore recommendable that a filter unit having been contacted with liquid is removed. In the embodiment described here the liquid sensor serves for the detection of an ingress of liquid or of an aerosol into the filter unit. Therefore, it is recommendable that the humidity sensor is arranged near the filter unit. When the humidity sensor reports the exceeding of a given limit value via the second electrical port and the first electrical port, an alarm signal is generated in the evaluation unit and/or the gas supply device is inactivated. Further, it is possible that the second hose portion is then automatically marked as "used", for instance by blocking the code element in the evaluation unit and/or writing a blocking code into the identity element.

Further, the invention relates to a device for insufflation of gas into a human or animal body, comprising a gas supply device with a gas port, to which a hose set according to the invention is connected by means of the first port, and comprising an insufflation device connected to the fourth port. Depending of the type of the hose set according to the invention, the gas supply device may be provided with an electrical port, to which the reading unit and/or the first electrical port of the hose set is connected in a detachable manner. It may also be provided that a receiver for receiving data transmitted by means of the transmitter of the hose set is comprised in the device.

A gas supply device usually comprises a connection to a gas source, for instance a carbon dioxide source, a pressure reducer, a flow meter, a pressure meter and a control/evaluation circuitry for controlling the pressure and/or the flow. It is understood that the mentioned components are connected to each other in a suitable way by means of gas lines (hoses or tubes). By means of the control circuitry, pressure and flow are adjusted by suitable setting elements. For this purpose, the control circuitry is connected with the flow meter and the pressure meter. For the purpose of the invention, further the reading unit can be connected with the control circuitry. To the control circuitry, further the humidity sensor may be connected. Finally, the control circuitry may electrically control a provided heating device.

BRIEF DESCRIPTION OF THE DRAWINGS

The invention is described in more detail by reference to the following figures, which represent an example of execution only:

FIG. 1 is a diagrammatical survey representation of a device for insufflation of gas according to the invention;

FIG. 2 is a detailed view of a hose set according to the invention in the section of the connecting elements in the embodiment comprising a thread;

FIG. 3 an axial direction is an axial view of connecting elements according to the invention comprising a bayonet lock; and FIG. 4 is a detailed view of two connecting elements comprising a latch connection.

DETAILED DESCRIPTION

In FIG. 1 can be seen a device 1 for insufflation of gas for the laparoscopy. As an insufflation instrument 8, a Veress needle is used, which is introduced during a medical operation into a human body. The gas supply device 23 comprises a connection 26 to a carbon dioxide source 27, a pressure reducer 28, a flow meter 29, a pressure meter 30 as well as a control circuitry and evaluation unit 31. The hose set is connected by means of a first port 3 with a gas outlet 32 of the gas supply device 23.

Further, a hose set according to the invention with a first hose portion 2 comprising a first port 3 and a second port 4 can be seen. The first port 3 and the second port 4 are connected with each other by a first hose 33. Further, a second hose portion 5 is provided, comprising a third port 6 and a fourth port 7, wherein the fourth port 7 can be connected to an insufflation instrument 8. Further, it can be seen that at the second port 4 a reading unit 19 is provided, which is connected by a wire connection and a contact pair 35 with the evaluation unit 31. An identity element 20 is arranged immediately opposite the reading unit 19.

The hose 33 is firmly connected with the second port 4. Equally, the hose 34 is firmly connected with the third port 6. Firmly connected means that the respective hose cannot easily be manually removed from the respective port. This also means that the second port and the third port do not represent separate constructional units, onto which a hose 33, 34 can manually be placed.

In FIG. 2, a detail view in the section of the second port and of the third port of a first embodiment of the invention is shown. The second port 4 comprises a first connecting element 9. The third port 6 comprises a second connecting element 10. At the third port 6, a sterile filter element 11 is provided, which spans the inner cross section of the third port 6. In the embodiment of FIG. 2, the connecting element 9 is formed by a flange 12 having a thread 13. The connecting element 10 also comprises a flange 14, which is however equipped with an external thread 15 being complementary to the internal thread 13. The connecting elements 9, 10 are connected with each other by a screw fit. Thereby, the sealing surfaces 35 come into contact with each other, thereby a gas-tight connection being obtained in the final position. Between the sealing surfaces 35, an elastomeric annular seal may also be used. In the final position, the reading unit 19 and the identity element 20 are immediately opposite to each other. This means that the two connecting elements 9 and 10 are turned into each other against the force of a(n) (elastomeric) sealing surface 35 or of the annular seal, until the reading unit 19 and the identity element 20 are opposite to each other, thereby always a defined assembly of the two connecting elements 9, 10 and a reliable sealing being secured. At the reading unit 19 or at the identity element 20, there may also be provided a stop element, the height of which is larger than the distance between the reading unit 19 and the identity element 20 in the final position, however smaller than this distance plus the height of one turn.

In the embodiment of FIG. 3, a so-called bayonet connection is provided, in lieu of the external thread 15 and of the internal thread 13. For this purpose, the connecting element 9 comprises a flange 12 with latching projections 16 being spaced to each other and projecting radially inwardly. The connecting element 10 also comprises a flange 14, being however provided with holding projections 17 extending in a radial direction. It is understood, as in the above embodiment, that the flange 14 has an external diameter, which is identical to or slightly smaller than the internal diameter of the flange 12. When the connecting element 10 is introduced into the connecting element 9 in such a manner that the holding projections 17 are disposed between the latching projections 16, the connecting element 10 can be turned relative to the connecting element 9 such that the holding projections 17 engage behind the latching projections 16. Herein it is recommendable that the latching projections 16 and/or the holding projections 17 are axially inclined in the peripheral direction and direction of rotation, such that the connecting element 10 during the introduction into the connecting element 9 is pulled into the latter in an axial direction. Thereby, the sealing surfaces 35 come into contact with each other in a sealing manner. It is not shown here that at the latching projections 16 and/or the holding projections 17 there may be provided with stop elements. These stop elements are arranged such that the reading unit 19 and the identity element 20 are immediately opposite to each other. In the shown embodiment, it may be recommendable that the latching projections 16 as well as the holding projections 17 are not uniformly distributed over the periphery, but are arranged in a non-symmetric manner. Thereby it is secured that the bayonet connection can be brought into engagement in only a single defined position of the connecting elements 9 and 10 relative to each other.

In FIG. 4 another variant of the invention can be seen, wherein the connecting element 10 is provided in the section of the periphery of the flange 14 with a latching recess 17. The connecting element 9 comprises in the section of the periphery of the flange 12 a latching element 18. Latching recess 17 and latching element 18 are complementary to each other. The latching recess 17 is arranged on an elastically bendable latching arm 36.

For the sake of simplicity, it is not shown in the figures that the second hose portion 5 comprises a humidity sensor and optionally a heating device. Both are contacted by contact pairs provided at the reading unit 19 and the identity element 20 and are connected with the control and evaluation unit 31.

What is claimed is:

1. A hose set for a device for insufflation of gas into a human or animal body, comprising:
    a first hose portion including a first port and a second port, said first port being connectable to an outlet of the device for insufflation, and a first hose connecting said first port and said second port, and
    a second hose portion including a third port and a fourth port, said fourth port being connectable to an insufflation instrument, and a second hose connecting said third port and said fourth port,
        wherein said first hose and said second hose are both external to the device for insufflation,
        wherein said second port comprises a first connecting element and said third port comprises a second connecting element, said first connecting element and said second connecting element being mechanically complementary with respect to each other, by means of said first connecting element and said second connecting element, said second port and said third port being connectable with each other in a gas-tight manner, wherein said first connecting element carries in a section of a periphery of its flange a first electrical port, and said second connecting element carries in a section of a periphery of its flange a second electrical port, wherein to said second electrical port a heating device arranged in said second hose portion is electrically connected, and
        wherein said second port or said third port comprises a sterile filter element, which spans the inner cross section of said second port or said third port, respectively.

2. The hose set according to claim 1, wherein the second connecting element carries the sterile filter element.

3. The hose set according to claim 1, wherein one of said first connecting element and said second connecting element is formed by a first flange with an internal thread and the other of said first connecting element and second connecting element is formed by a second flange with an external thread being complementary to said internal thread, and wherein said first and second flanges are connected with each other in a gas-tight manner by a screw fit in a final position.

4. The hose set according to claim 1, wherein one of said first connecting element and said second connecting element is formed by a first flange with latching projections being spaced to each other and projecting radially inwardly, and the other of said first connecting element and said second connecting element is formed by a second flange with holding projections extending in a radial direction, wherein said holding projections, relative to the peripheral direction of said second flange, have a distance, which is larger than the length of said latching projections, and wherein said holding projections and said latching projections are engageable with each other by rotating said first flange and said second flange against each other into a final position and connect said first and second flanges with each other in a gas-tight manner.

5. The hose set according to claim 1, wherein one of said first connecting element and said second connecting element is formed by a first flange having at least one latching recess provided in a section of the periphery of said first flange, and the other of said first connecting element and said second connecting element is formed by a second flange having at least one latching element provided in the section of the periphery, wherein said latching recess and said latching element are complementary with respect to each other and connect said first flange and said second flange with each other in a gas-tight manner by latching in each other into a final position.

6. The hose set according to claim 3, wherein one of said first connecting element and said second connecting element comprises a flange sleeve, the inner diameter of which is in the opening section larger than the outer diameter of said second flange of the other of said first connecting element and said second connecting element and wherein the inner diameter of the flange sleeve, relative to the direction of insertion of said second flange of said other of said first connecting element and second connecting element, reduces to an inner diameter, which is smaller than the outer diameter of said second flange of said other of said first connecting element and second connecting element, wherein at least one of the components, flange sleeve and/or second flange, is formed from a plastic or elastic material, or wherein one of said first connecting element and second connecting element comprises a flange sleeve with a cylindrical inner wall, wherein the outer diameter of said second flange, relative to the direction of insertion of said second flange of said other of said first connecting element and second connecting element, reduces from an outer diameter, which is larger than the inner diameter of the flange sleeve, to an outer diameter, which is smaller than the inner diameter of the flange sleeve, wherein at least one the components, flange sleeve and/or flange, are formed from a plastic or elastic material.

7. The hose set according to claim 1, wherein either said first connecting element, in the section of the periphery of its flange, or a gas supply, to which the hose set is connected, carries an electric reading unit, and said second connecting element, in the section of the periphery of its flange, carries machine readable identity element, wherein said identity element and said reading unit are arranged, in the final position of the two flanges, immediately opposite to each other.

8. The hose set according to claim 7, wherein with said first electrical port a wire connection for the connection to the device for insufflation and/or a transmitter for the wireless transmission of data to the device for insufflation, is electrically connected.

9. The hose set according to claim 7, wherein the identity element comprises a code element being different for every second hose portion, and wherein the identity element preferably comprises a safety element.

10. The device for insufflation of gas into a human or animal body, comprising a gas supply with a gas port, to which a hose set according to claim 1 is connected by means of said first port, and comprising an insufflation device connected to said fourth port.

11. The device according to claim 10, comprising an electrical port, to which said reading unit and/or said first electrical port of the hose set is connectable in a detachable manner, and/or comprising a receiver for receiving data transmitted by means of the transmitter of the hose set.

12. The method for insufflation of gas into at least one of a human and animal body, wherein the distal end of the insufflation device according to claim 10 is introduced into a body cavity, and gas is fed therethrough.

13. The method for multiple insufflation of gas into at least one of a human and animal body or into several different human and animal bodies, comprising the step of providing the device according to claim 10, wherein said first hose portion is not replaced after every insufflation process, and wherein said second hose portion is replaced after every insufflation process.

14. The hose set according to claim 1 further comprising a machine readable identity element carried in said section of said periphery of said flange of said second connecting element.

15. The hose set according to claim 14 further comprising a humidity sensor arranged in said second hose portion to which said second port is electrically coupled.

* * * * *